United States Patent [19]

Bodine, Jr.

[11] Patent Number: 5,060,638
[45] Date of Patent: Oct. 29, 1991

[54] ORTHOTIC AND RESTRAINING DEVICE POSITIONABLE ON THE HAND AND FOREARM

[75] Inventor: Robert C. Bodine, Jr., Mission Viejo, Calif.

[73] Assignee: Capra Resources, Inc., Mission Viejo, Calif.

[21] Appl. No.: 452,627

[22] Filed: Dec. 14, 1989

[51] Int. Cl.⁵ .......................... A61F 5/10; A61F 5/37
[52] U.S. Cl. .................................... 128/77; 128/845; 128/878; 297/466; 297/DIG. 4
[58] Field of Search ................. 128/75, 77, 87 R, 845, 128/846, 869, 878, 879; 269/328; 297/412, 414, 416, 466, DIG. 4

[56] References Cited

U.S. PATENT DOCUMENTS

| | | | |
|---|---|---|---|
| 2,693,794 | 11/1954 | Neville | 128/878 X |
| 3,287,064 | 11/1966 | Freeman | 297/466 |
| 3,640,273 | 2/1972 | Ray | 128/87 R |
| 3,746,332 | 7/1973 | Hakstian | 269/328 |
| 3,896,799 | 7/1975 | Seeley | 128/87 R |
| 3,903,878 | 9/1975 | Spann | 128/77 |
| 4,265,232 | 5/1981 | Stonich | 128/845 |
| 4,270,235 | 6/1981 | Gutmann | 269/328 X |
| 4,576,351 | 3/1986 | Brink | 297/416 |
| 4,660,550 | 4/1987 | Bodine | 128/77 |
| 4,730,801 | 3/1988 | Cloward | 128/77 X |
| 4,784,120 | 11/1988 | Thomas | 269/328 X |
| 4,930,842 | 6/1990 | Wilkinson et al. | 297/466 |
| 4,996,977 | 3/1991 | Tiedeken | 272/144 X |

OTHER PUBLICATIONS

Photocopies of 4 pages from Fred Sammons, Inc. Catalog.
Photocopies of 3 Pages from "Pictorial Reference Manual of Orthotics and Prosthetics", published by American Orthotics & Prosthetics Association.

Primary Examiner—Robert Bahr
Assistant Examiner—Linda C. M. Dvorak
Attorney, Agent, or Firm—Stetina and Brunda

[57] ABSTRACT

A hand and forearm orthotic device for attachment to the hand and forearm of chronically ill, elderly, handicapped, comatose or debilitated patients. The device comprises a block member, preferably formed of flexible foam or other soft material, said block member incorporating a retainer strap operative to hold a human forearm in a first position thereon. A hand support member is also connected to and/or incorporated in the block member so as to support the hand when the forearm is positioned on top of the block member. The hand support member may be adjustable so as to provide for varying degrees of movement or dorsiflexion of the hand. A longitudinal groove may be formed on the underside of the block member to facilitate placement of the block member on a wheelchair arm or other structure. One or more locking apparatus may be positioned within the longitudinal grooves so as to lock or deter removal of the block member from the wheelchair arm or other structure.

16 Claims, 3 Drawing Sheets

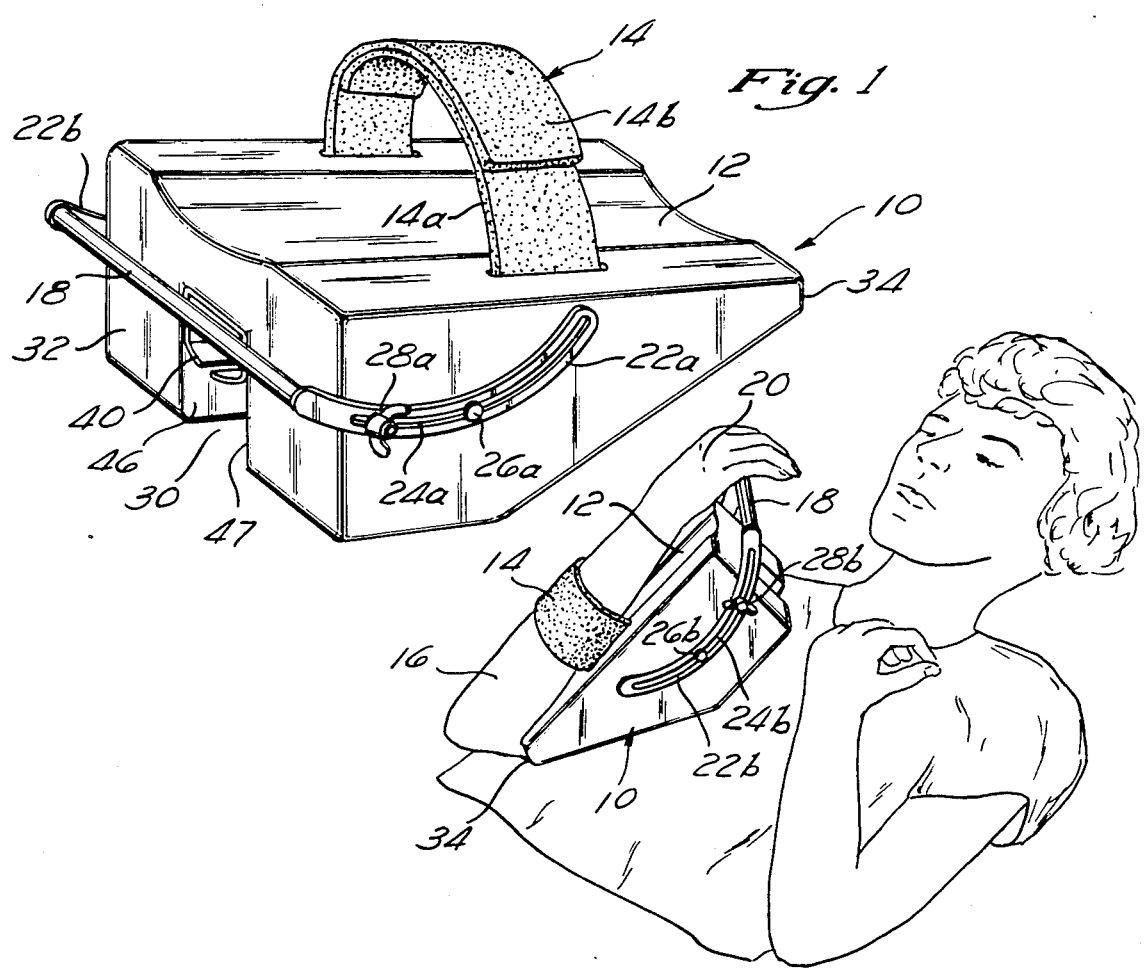
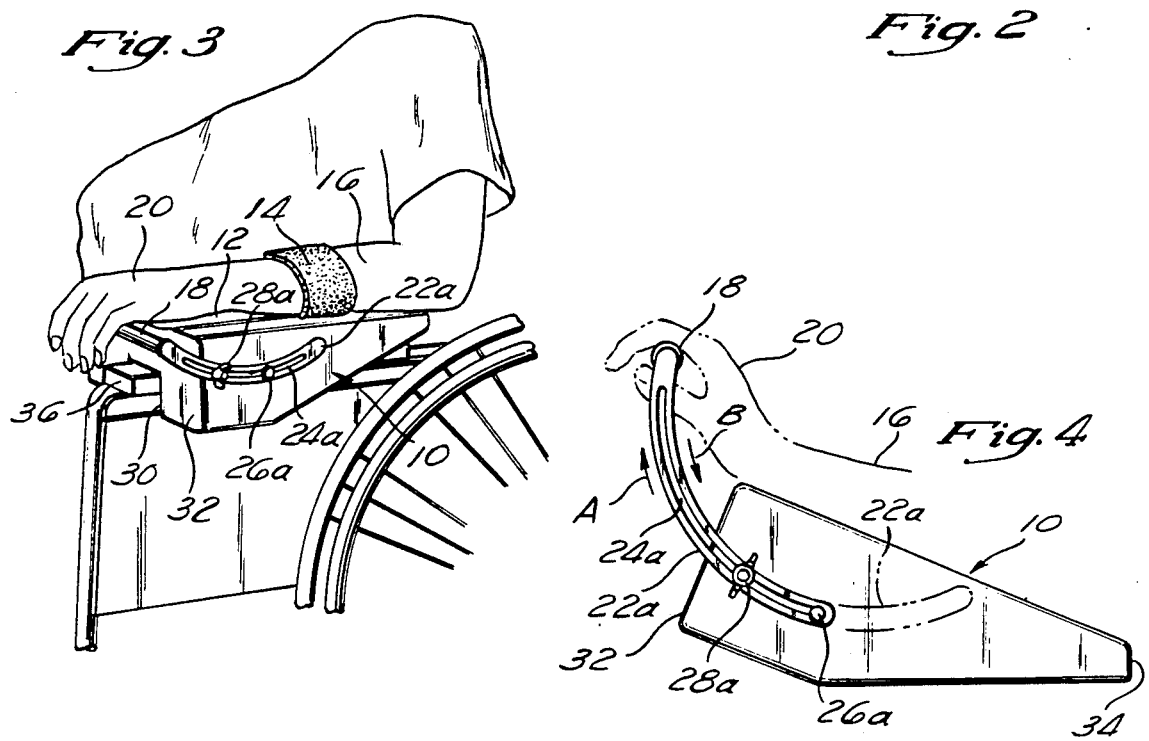

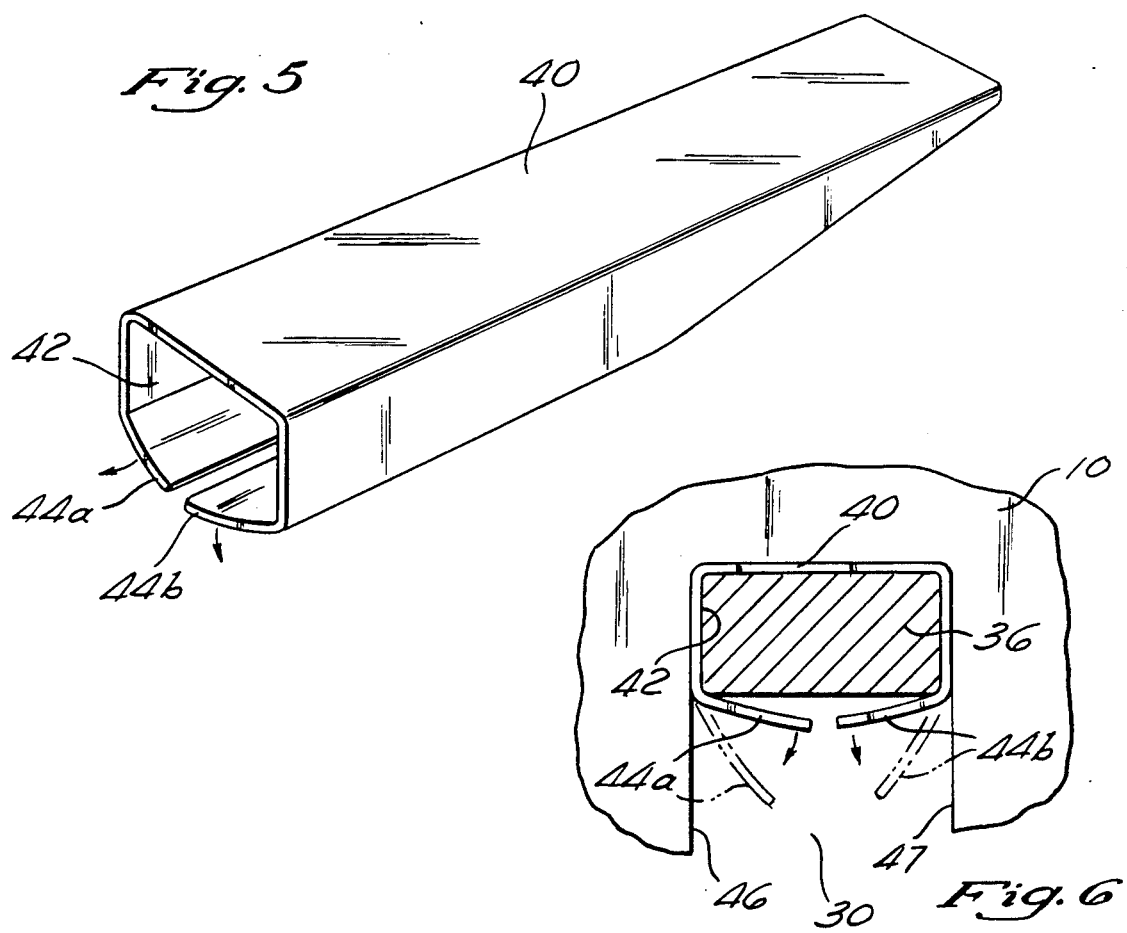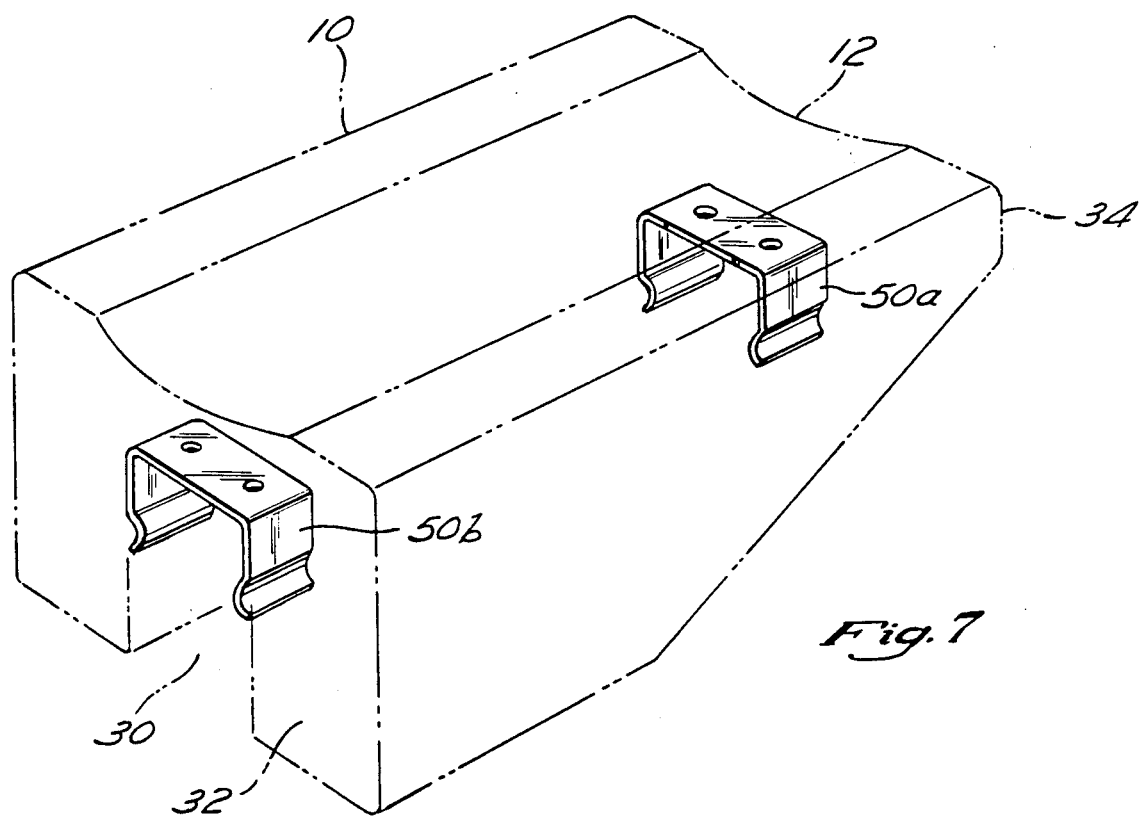

ORTHOTIC AND RESTRAINING DEVICE POSITIONABLE ON THE HAND AND FOREARM

FIELD OF THE INVENTION

The present invention pertains generally to medical equipment and more particularly to a device for restraining and shielding the forearm and hand and also for effecting orthosis of the entire pectoral limb including the hand, wrist, arm, elbow, and shoulder of patients who are ill, handicapped, elderly, or comatose.

BACKGROUND OF THE INVENTION

Chronically ill, elderly, severely handicapped, and/or comatose patients sometimes require restraint and/or cushioning of the hands and forearms to prevent self-injury and/or to maintain a posture which will prevent or minimize the development of muscular atrophy, edema, decubitus, and/or acute pressure sores.

Severely debilitated patients often tend to assume a posture wherein their arms become folded or retracted against the anterior thorax and/or shoulders. If such posture is allowed to remain uncorrected for an extended period of time, the muscles of the arms and shoulders will begin to atrophy. Additionally, the constant positioning of the patient's hands adjacent the anterior thorax often results in repeated scratching (i.e. fingernail trauma) of the chest and neck area.

Additionally, in some patients who remain comatose or bedridden for extended periods of time, a condition known as "wrist drop" (syn. carpoptasis, drop hand) may result. Wrist drop is a muscular atrophy due to paralysis or non-use of the extensor muscles of the hand and fingers.

Also, in some patients edema of the hands and wrists may develop if their hands and arms are not maintained in an elevated posture. This problem of edema formation is especially prevalent in patients whose cardiac function is compromised (e.g. edematous changes which result from congestive heart failure).

Those who provide care to chronically ill, elderly, severely handicapped, or comatose patients often undertake to restrain or affix the patient's arms in positions which will help to retain normal muscle tone and prevent accidental trauma. Such restraint is typically accomplished through the use of straps or tape. For example, the forearms of an elderly patient may be loosely taped or bound to the arms of a wheelchair so as to prevent the arms from falling into the spokes of the wheelchair wheels and becoming injured thereby. Also, to prevent patients from scratching or injuring themselves, it is common practice to cushion the hands or to place a pillow on the patient's chest and to allow the patient's arms to retract-against the pillow, thereby avoiding direct contact between the hands and the patient's body.

Although wheelchair "arm trays" and other orthotic appliances are available, such appliances are generally usable only in fixed locations (e.g., on the arm of a wheelchair) and do not generally attach to the patient's limb in a portable manner so as to permit the patient to move the limb about with the orthotic device remaining attached thereto.

Although these prior art methods and practices and devices may be somewhat helpful in preventing muscular atrophy, injury and/or edema, the common practice of taping or strapping the arms is known to be cumbersome and also tends to be somewhat imposing in appearance. Thus, there exists a need in the art for a simple device, attachable to the forearm, to effect restraint and shielding of the forearms/hands of a patient without the need for deployment of ties, cords, tapes, or the like. Additionally, it is desirable that such device be usable to accomplish orthosis of the entire pectoral limb, including the hand, wrist, arm, elbow, and shoulder.

SUMMARY OF THE INVENTION

The present invention accomplishes restraint, and shielding of the hand and forearm. Also, in certain applications, the device of the present invention will hold the hand and forearm on a slight incline or angle so as to prevent or minimize edema of the hand and wrist and/or the development of "wrist drop".

In accordance with the invention, there is provided a hand and forearm orthotic device comprising a block member having a hand support surface or member incorporated therein or attached thereto. At least one strap or other attachment means is provided to bind or hold a human being's forearm in proximity and/or contact with the upper surface of the block member.

Further in accordance with the invention, the block member may be shaped such that the distance from the upper surface to the underside of the block member is greater at the front end, than at the rear end of the block member. By such configuration, when resting on a generally flat underlying surface, the upper surface of the block member will be inclined such that, if a forearm is rested on the block member with the elbow of the forearm near the rear end of the block member and the hand near the front of the block member, the forearm will be elevated such that the hand is higher than the remainder of the forearm. In general, this configuration may be achieved by forming all or part of the block member in a general wedge-shape.

Still further in accordance with the invention, a trough may be formed in the upper surface of the block member. Such trough will be sized and configured to receive at least a portion of a human forearm therein, thereby facilitating resting of the forearm in a specific position on the upper surface of the block member.

Even further in accordance with the invention, a longitudinal groove or notch may be formed on the underside of the block member to facilitate placement of the block member over the top of a wheelchair arm or similar structure. One or more locking apparatus may be positioned within the longitudinal groove or notch so as to lock and/or hold the block member on the wheelchair arm or other structure, thereby preventing inadvertent removal therefrom.

Even further in accordance with the invention, the hand support surface or member may comprise a generally cylindrical hand grip or other structure adjustably attached to the block member so as to permit varying degrees of dorsiflexion of the hand.

Still further in accordance with the invention, at least the outer surfaces cf the block member may be formed of soft material such as flexible or semirigid plastic foam (e.g. flexible, closed cell, polyethylene foam) which is sufficiently soft and flexible to prevent injury to the body of the wearer when the device is thrust or rubbed against the anterior thorax, neck or other parts of the body. Additionally, the internal construction of the device may comprise one or more rigid inserts or members to impart the rigidity and structural integrity necessary for the device to carry out the various functions, actions, and uses described herein.

One object of the invention is to provide a device for restraining and shielding the hand and/or forearm of a chronically ill, elderly, handicapped, debilitated, or comatose patient.

A further object of the invention is to provide a device which will effect orthosis of the entire pectoral limb including the hand, wrist, arm, elbow, and shoulder.

A further object of the invention is to provide a hand and forearm restraining device which is attachable to the arm of a wheelchair or similar object so as to hold the hand and forearm in a slightly inclined or elevated position so as to prevent muscular atrophy, edema, wrist drop, and associated conditions.

Yet another object of the invention is to provide a device which may be used to achieve abduction of the shoulder in ill, elderly, handicapped, debilitated, or comatose patients.

A still further object of the invention is to provide a device which may be used to correct or treat severely contracted elbows in ill, elderly, handicapped, debilitated, or comatose patients.

An even further object of the invention is to provide a hand and forearm shielding device which permits the patient to maintain mobility of the arm(s) but which will prevent the patient from scratching or otherwise injuring the anterior thorax, neck, or other regions of the body as may occur if the unrestrained and unshielded hands are positioned thereagainst.

Further objects and advantages of the invention will become apparent to those skilled in the art upon reading and understanding of the following description and the accompanying drawings.

BRIEF DESCRIPTION OF THE DRAWINGS

FIG. 1 is a perspective view of a first embodiment of a preferred device of the present invention;

FIG. 2 is a perspective view of a human being having the first embodiment of the preferred device of the present invention positioned on her right forearm and hand;

FIG. 3 is a perspective view of a first embodiment of a preferred device of the present invention being utilized to maintain a desired placement of the forearm and hand of a patient while the patient is seated in a wheelchair;

FIG. 4 is a side elevational view of a first embodiment of a preferred device of the present invention, showing the adjustability of the handle portion thereof;

FIG. 5 is a perspective view of a wheelchair arm gripping insert positionable on the underside of the device of the present invention;

FIG. 6 is a cross-sectional view of a portion of the device of the present invention having the wheelchair arm gripping insert of FIG. 5 mounted therein;

FIG. 7 is a perspective view of alternative wheelchair arm gripping apparatus comprising a plurality of clamps mounted within the longitudinal groove formed on the underside of a device of the present invention;

DETAILED DESCRIPTION OF A PREFERRED EMBODIMENT

Figure 8:
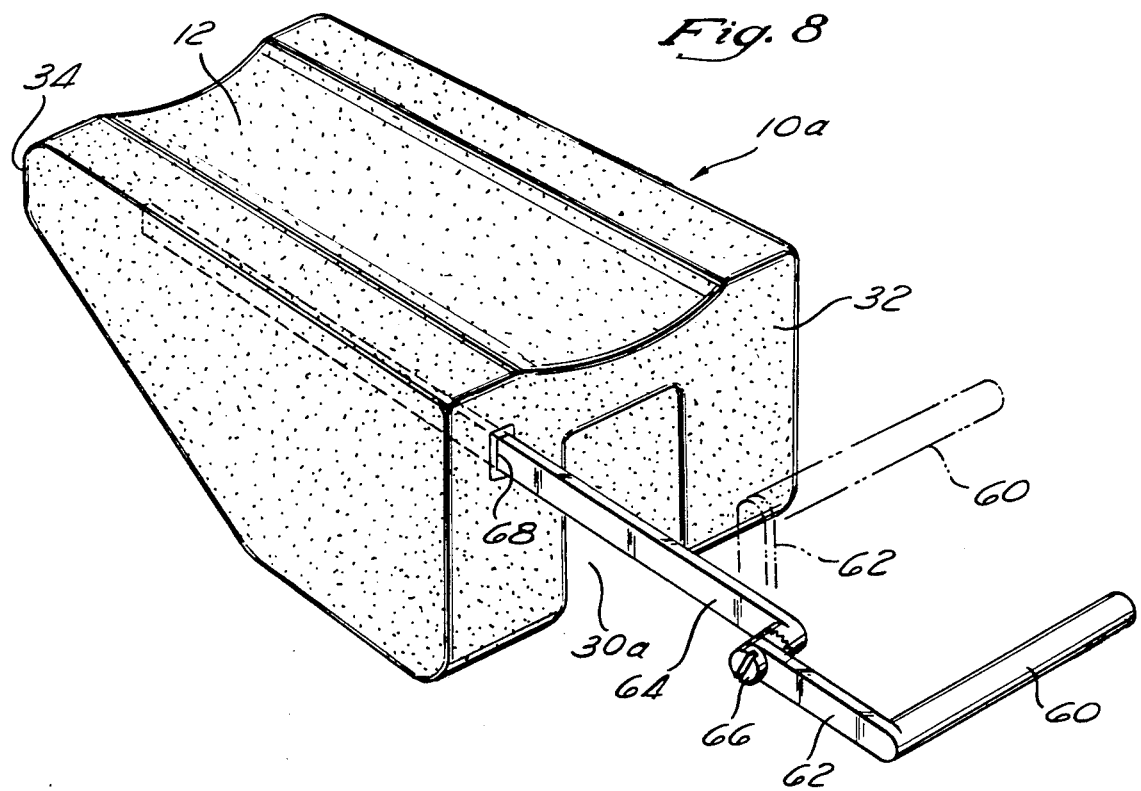
FIG. 8 is a perspective view of a second embodiment of the device of the present invention.

The following detailed description and the accompanying drawings are intended for purposes of describing and illustrating a preferred embodiment of the present invention and are not intended to limit the scope of the invention in any way.

A presently preferred device of the present invention comprises a partially wedge-shaped block member 10. The block member 10 may be formed of any materials which will enable the block member to achieve the uses, functions, and applications herein described. It is preferable that, at least the outer surfaces of the block member 10 be formed of material which is sufficiently soft to avoid the likelihood of injury to the wearer's body. At the same time, the block 10 should exhibit sufficient internal structural integrity and rigidity to carry out the hereinafter described functions of the device of the present invention. Such combination of structural integrity and surface softness may be achieved by forming the core of the block of a rigid (e.g. solid plastic, metal) material and providing a soft outer covering (e.g. flexible/resilient plastic foam) formed on at least some of the outer surfaces of the rigid core.

A slight trough 12 is formed longitudinally in the upper surface of the block member 10 so as to permit the forearm of a human being to rest comfortably within such trough 12. The trough 12 may be molded into the overall configuration of the block member 10 or may be subsequently cut or machined away after the block member 10 has been preformed with a substantially flat upper surface.

A retainer strap 14 is provided to hold the forearm of a patient firmly yet comfortably within the trough 12 of the upper surface of block member 10. The retainer strap 14 consists of first 14a and second 14b strap members, each connected at one end to a lateral side of the block member 10 and joinable over the center portion of the upper surface thereof. A hook and loop connector material (e.g. Velcro TM) or any other suitable type of connector may be used to releasably join the first 14a and second 14b strap members in the manner shown in FIG. 1.

Thus, when the forearm 16 of a patient is placed on the upper surface of the block member 10, the retainer strap 14 may be securely fastened over the top of the forearm 16 thereby holding the forearm 16 of the patient in position on the upper surface of the block member 10.

In the first embodiment shown in FIGS. 1-4, a hand support 18, such as a cylindrical, rod-like hand grip or member, is attached to the block member 10 in such position as to provide a resting point or support structure for the hand 20 of the patient when the forearm 16 is in its desired position on the upper surface of the block member 10. (FIGS. 2 and 3). The hand support 18 may be adjustable so as to provide for adjustment and moveability of the position of the hand 20 and the attitude or bend of the wrist joining the hand 20 to the forearm 16. Specifically, the hand support 18 may be adjusted to provide varying degrees of dorsiflexion of the hand. By providing for such adjustable movement of the hand support 18, it is possible to periodically adjust or alter the position of the hand, thereby avoiding muscular atrophy and/or the development of wrist drop or other associated conditions.

Additionally, one or more sleeves of material, such as resilient plastic foam, may be disposed around the hand support 18 to alter the diameter of the hand support 18 as desired.

In the first preferred embodiment shown in FIGS. 1–4, the adjustability of the hand support 18 is achieved through the use of arcuate mounting members 22a, 22b attached to opposite ends of the hand support 18. The arcuate mounting members 22a, 22b extend adjacent to, and on either side of the block member 10. Each arcuate mounting member 22a, 22b has an arcuate slot 24a, 24b formed therein. Pin members 26a, 26b extend through the slots 24a, 24b and are anchored in the sides of the block member 10. The heads of pin members 26a, 26b are generally larger than the width of the slots 24a, 24b to prevent the arcuate mounting members 22a, 22b from being pulled laterally away from the sides of the block member 10. Additionally, secondary threaded pin members extend through the slots 24a, 24b, having wing nuts 28a, 28b mounted thereon. When the wing nuts 28a, 28b are loosened, the hand support 18 may be moved upwardly (arrow A) or downwardly (arrow B), thereby slidably moving the arcuate mounting members 22a, 22b relative to the pins 26a, 26b disposed therethrough. When the hand support 18 is disposed in a desired position, the wing nuts 28a, 28b are then tightened to hold the arcuate mounting members 22a, 22b and the hand support 18 in a fixed position. The hand support 18 is thereby securely held in a desired position until such time as the wing nuts 28a, 28b are once again loosened to permit readjustment of the position of the hand support 18.

Figure 9:
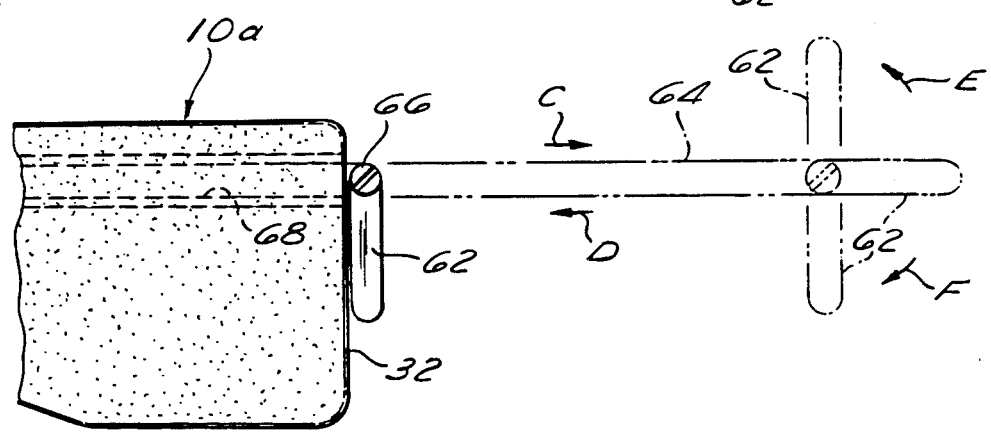
FIG. 9 is a side elevational view of a portion of the second embodiment of the preferred device of the present invention.

In the second embodiment shown in FIGS. 8 and 9, the hand support comprises a first extension member 62 and hand grip 60, pivotally mounted on the distal end of an elongate member 64 by way of locking screw 66. The elongate member 64 is inserted, proximal end first, into a channel (dotted lines) which extends longitudinally within block member 10a. Such channel opens through an aperture 68 formed in the front edge of the block member 10a such that the elongate member 64 may be slidably advanced out of (arrow C) or into (arrow D) the internal channel (dotted lines) through aperture 68. Such slidable extension/retraction (arrows C/D) of the elongate member 64 enables the user to adjust the distance between the front edge of the block 10a and the hand grip 60. Any suitable type of stopping or holding means (e.g. frictional engagement of the elongate member with the surrounding walls of the channel, set screws, etc. . . . ) may be employed to hold the elongate member at a desired point of extension relative to the front edge of the block member.

Additionally, the position of hand grip 60 is rotationally adjustable about screw 66. When screw 66 is loosened, the hand grip 60 and attendant perpendicular first extension member 62 may be rotated to various positions above and below the plane of the telescoping member 64 (arrows E and F). When the desired position of the hand grip 60 has been attained, the screw 66 is tightened to hold the first extension member 62 and the hand grip 60 in such desired position.

Additionally, as in the first embodiment, the diameter of the hand grip 60 may be adjusted by providing sleeves of various thickness positionable about the exterior of the hand grip 60. Such sleeves may be formed of elastomeric material, resilient plastic foam, or any other material known to be usable in such application.

A groove, notch, or furrow 30 may be formed longitudinally on the underside of the block member 10 or 10a of either the first or second embodiment of the invention. As shown, the groove 30, 30a comprises a generally rectangular notch or cutaway region which extends longitudinally, from the front end 32 to the rear end 34 of the block member 10, 10a. The groove 30, 30a is specifically sized and configured to receive the armrest 36 of a wheelchair therein. It is preferable that the arm 36 of the wheelchair fit snugly within the groove 30, 30a such that the block member 10 or 10a will rest evenly on the upper surface of the armrest 36 without falling, or being easily removed, therefrom.

Additionally, one or more locking apparatus may be positioned within the groove 30, 30a to look or retain the block member 10 on the armrest 36 of the wheelchair. A first preferred locking apparatus shown in FIGS. 5 and 6 comprises an insertable member 40 comprising hollow, channel-like structure having an open inner region 42 with bendable leaflets 44a, 44b extending generally downward from the underside thereof. The member 40 is inserted or otherwise positioned within the groove 30 on the underside of the block member 10 and firmly affixed to the block member 10. It is generally desirable that the member 40 extend the entire length from the front end 32 to the rear end 34 of the block member 10. The leaflets 44a, 44b may then be grasped at either end of the groove 30, by the user, and bent downwardly so as to be in abutment and/or close spacing with the side walls 46, 47 of the groove 30. This will permit the member 40 to be passed downwardly over the armrest 36 of a wheelchair such that the armrest 36 will reside within the inner region 42 of the member 40. The leaflets 44a, 44b are then released, allowing them to resiliently or otherwise to return to their original closed, unextended or biased configuration as shown in FIGS. 5 and 6. In such closed or unextended configuration, the leaflets 44a, 44b will frictionally engage the underside of the wheelchair armrest 36, thereby preventing the block member 10 from being lifted upwardly from or removed from the wheelchair arm member without sufficient force to overcome the bias of the leaflets 44a, 44b. The force necessary to overcome the upward bias of the leaflets 44a and 44b will, preferably, be such that the average elderly or other wheelchair patient would be unable to muster sufficient upward lifting force to release the block from the wheelchair armrest 36 after it has been properly positioned thereon. Additionally, it is preferable that the inner channel 42 of the member 40 be sized to accommodate the armrest 36 of the wheelchair without excessive free space that would permit the block member 10 to move from side to side or otherwise undergo undesirable movement when positioned on the arm of the wheelchair.

It will be appreciated that, in addition to the first preferred member 40, shown in FIGS. 5 and 6, many other types of clips, straps, clamps, and gripping members may also be employed to hold the block member 10 on the arm of a wheelchair. For example, as shown in FIG. 7, clamp members 50a, 50b may be positioned within the groove 30 on the underside of the block member 10. Such clamp members may comprise plastic, steel, or other material having sufficient memory or resiliency to permit the clamp members to be frictionally passed over the armrest 36 of the wheelchair and to clamp thereonto, thereby holding the armrest of the wheelchair in position within the groove 30 of the block member 10. It is desirable that the pressure required to spread each clamp member 50a, 50b sufficiently to clear and pass the sides of the wheelchair arm 36 will be sufficiently great to preclude the average elderly person or wheelchair bound patient from pulling block 10 away from the wheelchair arm 36 after it has been clamped thereonto.

The foregoing description is intended only to illustrate presently preferred embodiments of the present invention, and does not serve to limit the invention in any way. Since numerous modifications and changes will readily occur to those skilled in the art, the foregoing description and the claims which follow shall not be construed as being limited to the exact embodiments shown. Rather, it is intended that all suitable modifications and changes to the above-described embodiments be construed as coming within the scope of the following claims and the equivalents thereof.

What is claimed is:

1. A hand and forearm orthotic device comprising:
   a block member having a front end, a rear end, an inclined upper surface, and a generally flat underside;
   a retainer strap operative to hold a human forearm in a first position on the upper surface of said block member;
   a hand support member attached to the block member and extending forward of the front end of said block member to engage the hand when said forearm is in said first position;
   said block member being shaped such that the upper surface to underside dimension at the front end of said block member is greater than the upper surface to underside dimension at the rear end of said block member such that when the generally flat underside of the block member is positioned on a horizontally planar underlying surface the forearm in said first position on the upper surface of the block member will be inclined such that the wrist is higher than the elbow; and
   said hand support member being movably mounted to said block member and having rigid means for selectively adjusting the position of said support member relative to said block member so as to effect varying degrees of dorsiflexion of the hand when said forearm is in said first position.

2. The orthotic device of claim 1 wherein said block member is at least partially wedge-shaped.

3. The orthotic device of claim 1 wherein a trough is formed in the upper surface of said block member, said trough being sized and configured to receive at least a portion of a human forearm therein.

4. The orthotic device of claim 3 wherein said retainer strap comprises first and second strap members connectable, to one another to form a generally arcuate retainer strap for holding the forearm against the upper surface of the block member.

5. The orthotic device of claim 1 further comprising a longitudinal groove formed in the underside of said block member, said longitudinal groove being sized and configured to receive the arm of a wheelchair therein such that said block member will rest stably on said wheelchair arm.

6. The orthotic device of claim 5 wherein said underside groove comprises a generally rectangular notch having first and second vertical side walls and an upper surface.

7. The orthotic device of claim 6 wherein the upper surface of said notch is slanted such that, when positioned on the arm of a wheelchair, the block member will rest in a slightly inclined position, such that when a forearm is positioned on the upper surface of said block, the hand will be elevated above the forearm.

8. The orthotic device of claim 5 further comprising a locking apparatus positioned within said longitudinal groove to substantially hold the block member on a wheelchair armrest.

9. The orthotic device of claim 8 wherein said locking apparatus comprises:
   first and second leaflets, biased to a first closed position, but openable to a second open position,
   said leaflets, when in said second open position, being spaced sufficiently far apart to permit passage of a wheelchair armrest therebetween and, when in said second closed position, being sufficiently close together to substantially prevent passage of said wheelchair armrest therebetween.

10. The orthotic device of claim 8 wherein said locking apparatus comprises at least one clip, operative to frictionally engage the armrest of a wheelchair.

11. The orthotic device of claim, 1 wherein said block member is made of flexible plastic foam.

12. The orthotic device of claim 1 wherein said at least a portion of said block member is made of plastic foam.

13. The orthotic device of claim 1 wherein said block is made of substantially closed cell polyethylene foam.

14. The orthotic device of claim 1 wherein said block member comprises a generally rigid core having a soft outer cover disposed thereon.

15. The orthotic device of claim 1 wherein said block member comprises a rigid plastic core with a flexible plastic foam outer cover disposed thereon.

16. The orthotic device of claim 1 wherein said hand support member further comprises:
   at least one arcuate attachment member movably mounted to said extending forward of the front end of said block member; and
   at least one hand support element attached to said arcuate attachment member, said at least one hand support element being sized, configured and positioned to engage and support the patient's hand forward of the front end of said block member when the forearm is in said first position;
   said arcuate attachment member being adjustably movable relative to said block member to adjust the degree of dorsiflexion of the patient's wrist when the forearm is in said first position.

* * * * *